United States Patent [19]  
Feld

[11] Patent Number: 4,603,220  
[45] Date of Patent: Jul. 29, 1986

[54] PROCESS FOR THE PREPARATION OF AROMATIC MONOCARBOXYLIC ACIDS FROM TOLUENE AND SUBSTITUTED TOLUENES

[75] Inventor: Marcel Feld, Cologne, Fed. Rep. of Germany

[73] Assignee: Dynamit Nobel AG, Troisdorf, Fed. Rep. of Germany

[21] Appl. No.: 632,261

[22] Filed: Jul. 18, 1984

Related U.S. Application Data

[63] Continuation of Ser. No. 397,710, Jul. 13, 1982, abandoned.

[30] Foreign Application Priority Data

Jul. 16, 1981 [DE] Fed. Rep. of Germany ....... 3128147

[51] Int. Cl.$^4$ .............................................. C07C 51/265
[52] U.S. Cl. ..................................... 562/416; 562/414
[58] Field of Search ................. 562/414, 416, 473, 494

[56] References Cited

U.S. PATENT DOCUMENTS 4,314,073 2/1982 Crooks ................................. 562/416
4,330,676 5/1982 Moxham .............................. 562/416

FOREIGN PATENT DOCUMENTS 0002749 7/1979 European Pat. Off. .

Primary Examiner—Natalie Trousof
Assistant Examiner—Patricia M. Scott
Attorney, Agent, or Firm—Felfe & Lynch

[57] ABSTRACT

In a process for preparing aromatic monocarboxylic acids by oxidation of toluene or of toluenes substituted in the nucleus, the starting substances are reacted in the liquid phase with oxygen or with a gas containing oxygen, at a temperature of 80°–180° C. and a pressure of 5 to 50 bar in the presence of acetic acid as diluent and a soluble cobalt and/or manganese salt in combination with a bromide, and the aromatic monocarboxylic acids are then obtained by solid-liquid separation of the cooled reaction mixture.

To reduce the dimensions of the oxidation reactor, for which particularly corrosion-resistant materials are necessary, and to isolate the target products in high yield and purity, as well as to reduce the technical complexity and cost of the treatment of the amounts of solvents that are yielded, relatively small amounts of acetic acid are used as solvents or diluents, namely at a ratio by weight of the alkyl aromatic being oxidized and acetic acid of 0.5:1 to 6:1. Not until the reaction has ended is the dilution, which is necessary for the isolation of the target product by solid-liquid separation of the cooled reaction mixture, performed by the addition of dilute aqueous acetic acid or of the washing filtrate from a preceding oxidation run. A typical example is the preparation of p-tert-butylbenzoic acid from p-tert-butyltoluene by the method described.

14 Claims, No Drawings

PROCESS FOR THE PREPARATION OF AROMATIC MONOCARBOXYLIC ACIDS FROM TOLUENE AND SUBSTITUTED TOLUENES

This application is a continuation, of application Ser. No. 397,710, filed July 13, 1982.

DESCRIPTION

The invention relates to a process for the preparation of aromatic monocarboxylic acids by oxidation of toluene or of toluenes substituted on the nucleus.

Appropriate starting substances are, in addition to toluene, substituted toluenes having one or more identical or different substituents which are very stable under the conditions of the reaction, such as for example halogens, aryl groups, nitro groups, alkoxy groups, aryloxy groups and tertiary alkyl groups.

The process is characterized by the fact that the conditions of the reaction and subsequent operations are coordinated such that, even when the target product has a relatively high solubility in acetic acid, or if the starting product is of comparatively low purity, the aromatic carboxylic acid can be obtained by a technically very simple method in relatively high yield and high purity.

Numerous methods are known for the oxidation of methyl groups in the aryl position with atmospheric oxygen using, heavy metal salts, especially cobalt salts as catalyst, bromides as co-catalyst, and acetic acid as a solvent. Since the reactivity of the methyl group is influenced by additional substituents on the aromatic compound, there are a variety of different, optimum oxidation conditions for variously substituted toluenes. Consideration is given to this in a number of methods given for preparing substituted benzoic acids, by the selection of appropriate parameters such as temperature, pressure, catalyst composition and concentration. While the necessary attention should be paid to suitable reaction conditions in planning these oxidation processes, insufficient heed is paid to the matter of achieving the simplest possible, productive processing of the reaction mixtures, which is equally important to the yield and purity of any technical production process, especially in those cases involving the production of benzoic acids which are relatively easily soluble in acetic acid. Above all, however, the reaction conditions in the known processes are not adapted to the need for an easy and economical method for the preparation of the finished product.

THE INVENTION

The present invention describes a technically simple general process for the oxidation of toluene and substituted toluenes and for the isolation of the monocarboxylic acids resulting as target products. This process consists of the oxidation, with oxygen or an oxygen-containing gas, especially air, at an elevated pressure of 5 to 50 bar and a temperature of 80° to 180° C., in the presence of acetic acid, of a soluble cobalt salt and/or manganese salt (which can be used if desired with an additional heavy metal catalyst) and of a bromide, wherein the heavy metal catalyst and the alkyl aromatic are used in the molar ratio of 0.003:1 to 0.02:1 and the bromide and the heavy metal catalyst in the molar ratio of 0.5:1 to 2:1.

The process of the invention is characterized by an especially high concentration of the alkyl aromatic or by an especially low concentration of acetic acid in the starting mixture in which the alkyl aromatic and acetic acid are used in a ratio by weight of 0.5:1 to 6:1, and in most of the processes preferably in the weight ratio of 1:1 to 3:1. The weight ratio of alkyl aromatic and acetic acid that is preferred within the limits stated above depends on the solubility of the target product and on the nature of the starting product, i.e., on the tendency of the starting, intermediate and end products to undergo secondary reactions under the reaction conditions that are necessary in each case. As an important characteristic of the process of the invention, it is not until the oxidation has ended that dilution with an appropriate solvent, which is necessary for the separation of the target product from the reaction mixture or advantageous for the achievement of a high yield and purity of the target product is performed. It is especially advantageous to use for the dilution of the reaction mixture all or part of the wash filtrate from a preceding identical oxidation run.

The advantageous use of the relatively low acetic acid concentration during the oxidation is not suggested by known processes, and is even contradictory to the teaching conveyed by a number of patents. It is stated several times in the literature that great concentrations of water are undesirable in the catalytic air oxidation of alkyl aromatics. According to German Offenlegungsschrift No. 1,768,899, the weight ratio of water to acetic acid should not be greater than 1:9, and, according to German Auslegesqhrift No. 1,418,852, even a water content exceeding 0.05 weight parts per weight part of acetic acid can result in the interruption of the oxidation.

Interference with the oxidation by water is all the more of a problem as water increasingly forms as an oxidation by-product as oxidation progresses. In order insofar as possible to avoid the undesirable influence of water, the acetic acid serving as solvent in the catalytic air oxidation of alkyl aromatics is used in a relatively high concentration with respect to the starting product that is to be oxidized. This corresponds to the teaching conveyed, for example, by German Offenlegungsschrift No. 1.768,899, German Auslegeschrift No. 1,418,852 and Japanese patent 33,670/77. To reduce the water concentration, however, it is also possible, as described for example in Japanese patent 41,253 77, to oxidize in the presence of acetic anhydride, or else to distill out part of the reaction water during the oxidation, analogously to German Offenlegungsschrift No. 1,768,899 and 2,436,177.

The conventional use of relatively great amounts of solvent in the oxidation stage of the production of aromatic monocarboxylic acids by an air oxidation of alkyl aromatics catalyzed by heavy metals and bromides in an acetic acid solution results in considerable disadvantages in many respects. For example, the amount of solvent used during the oxidation is one of the factors that determines the dimensions of the reactor, for which particularly corrosion-resistant materials, preferably titanium, are necessary. On the other hand, high-grade steel is adequately corrosion-resistant for the crystallization vessels, which are less subject to such corrosion. From this point of view, a reactor of smaller dimensions for the same capacity of production would be very advantageous.

However, more decided disadvantages are involved in the use of relatively great amounts of acetic acid in the technical processing of the reaction mixtures. Many aromatic monocarboxylic acids, such as benzoic acid, o-chlorobenzoic acid, m-nitrobenzoic acid, p-tert-butylbenzoic acid or anisic acid, are easily soluble in acetic acid. This makes the isolation of the target products in a high yield considerably more difficult. The simple filtration of the reaction mixtures after cooling them to room temperature would result in considerable losses of yield. To reduce these losses, the reaction mixture must, in the simplest case, be concentrated prior to the isolation of the target product. In a case where the target product has an especially high solubility, however, this alone would not be enough, because great product losses would occur even in the necessary washing of the filter cake with acetic acid. In this case, then, a second solvent would have to be used for washing the filter cake, or else the washing filtrates would have to be treated separately for the recovery of the dissolved product. In both cases the treatment of the washing filtrates would involve considerable expense.

Even in the production of aromatic monocarboxylic acid that is less soluble in acetic acid, one of the factors determining the technical complexity and cost of the processing is the amount of solvent, since the filtrates have to be distilled for the separation of the water of reaction and the recovery of the acetic acid.

The problem at which the invention is directed are solved by the process as described in detail below. This process overcomes prior art disadvantages in a number of ways. For example, inspite of the often confirmed undesirable influence of great concentrations of water, it has surprisingly been found that, in the catalytic air oxidation of toluene or toluenes substituted in the nucleus by the method of the invention, aromatic monocarboxylic acids are obtained in high yield and high purity if relatively small amounts of acetic acid are used as solvent or diluent. For example, toluene oxidation has been accomplished even at a molar ratio of toluene to acetic acid greater than 1, the molar ratio of reaction water to acetic acid being greater than 1 after the virtually complete reaction of the toluene.

The advantages of the process of the invention with regard to the yield obtained even in the case of target products of relatively good solubility and even though the working up of the reaction mixtures is easily performed technically, are so great that even the possible disadvantages of the very low solvent concentration during the oxidation, in the form of slightly intensified secondary reactions, become insignificant if they occur at all. The deciding factor in a technical process is not the absolute amount of the target product that is formed, but the amount that is the most favorable from the economic viewpoint, i.e., the amount that can be isolated by the simplest possible method. In the process of the invention, the reaction conditions in which a relatively very small amount of solvent is used fulfill the need for a technically very simple separation and purification of the end product.

The isolation of the target product is accomplished in the process of the invention by a simple filtration by one of the known filtration methods, such as the use of a filter centrifuge for example. Even in cases of target products of relatively good solubility, there is no need for the costly prior concentration of the reaction mixture, or for a second filtration of product from concentrated mother liquor, much less a complete change of the solvent.

In the process of the invention the acetic acid concentration during the reaction is made so low that, for the isolation of the target product from the cooled reaction mixture by one of the conventional filtration methods, it is necessary first to dilute the mixture with 0.2 to 10, preferably 0.5 to 5, weight-parts of a suitable solvent or solvent mixture per weight-part of acetic acid used in the reaction. The conditions of the reaction mixture dilution as regards temperature and amount of the diluent are to be product takes place as a result, or such that any product that is precipitated is redissolved by subsequent temperature elevation. In the case of an easily soluble target product, after the dilution is performed the latter should be very completely dissolved at elevated temperature, and should not crystallize out until the subsequent cooling down to room temperature or to a temperature lower than room temperature but above the solidification point of the mother liquor. Poorly soluble by-products can then be separated, if desired, by filtration of the hot reaction solution.

Even though the advantages of the process of the invention are especially apparent in the production of those aromatic monocarboxylic acids which are relatively easily soluble in acetic acid and therefore are also found in dissolved form in the diluted, hot reaction mixture, the process is nevertheless not limited to such cases, but can also be used successfully and advantageously for the preparation of less easily soluble benzoic acids that are present in the hot, diluted reaction mixture in largely undissolved form.

For the dilution of the reaction mixture after completion of the reaction, as required in the described process for the isolation of the target product in high purity from a mixture that is still fluid at room temperature, there are basically a number of possibilities. And it can be considered to be an additional advantage of the process of the invention that the diluent does not have to satisfy any requirement of resistance to oxidation or of being one that does not inhibit reaction under oxidation conditions. The only requirement would be that it does not react with a product in the reaction mixture under the processing conditions, does not impede the processing, and does not have an adverse effect on the yield and purity of the target product.

With these considerations in mind, the diluents would be, for example, low-molecular aliphatic or aromatic hydrocarbons, halogenated hydrocarbons, esters, ketones, nitriles and also more poorly esterifiable alcohols. On account of the possibility of a virtually free selection of the appropriate diluent, the process can be very well adapted to the special conditions created by the nature of the impurities and the solubility of the target product.

Despite this advantageous, broad selection of the appropriate diluent, in the preferred form of the process of the invention, a dilute aqueous acetic acid is used for the dilution of the reaction mixture in consideration of the distillative processing of the aqueous acetic acid mother liquor. The decisive advantage of this process then results from the possibility of performing the dilution of the reaction mixture with the washing filtrate from a preceding oxidation run of the same kind, which is virtually saturated with target product.

The two-time use of a considerable part—often even the greater part—of the total amount of solvent required, first for the washing of the target product, and then as washing filtrate for the dilution of the reaction mixture of a subsequent run, is advantageous in several ways. In the cases of easily soluble target products, such as for example benzoic acid, m-nitrobenzoic acid, o-chlorobenzoic acid, p-tert-butylbenzoic acid or anisic acid, the yield losses due to dissolution are greatly reduced by this measure. This is true especially when, due to the use of a starting product of low purity or to considerable secondary reactions, an especially thorough washing of the target product is necessary. A high purity is required precisely in the case of the aromatic monocarboxylic acids used as preservatives for foodstuffs and for the production of drugs and dyes, and for other purposes.

The requirement for high purity in the carboxylic acids obtained by catalytic air oxidation of alkyl aromatics necessitates, even in the simplest case, a thorough washing out of the target products isolated from very great amounts of solvents to remove catalyst residues and by-products. Not only must attention be paid to by-products in the case of a starting product of low purity, but basically they cannot be completely suppressed in the reaction running radically through several stages.

The isolation of the target product from a large amount of solvent with the simultaneous use of greater amounts of washing liquid results, even in the case of a substituted benzoic acid that is less easily soluble in acetic acid, such as for example p-nitro-, p-chloro- or p-phenoxybenzoic acid, in decided losses of yield. In the case of more easily soluble target products, the process becomes uneconomical on account of an excessively low yield or excessively complicated separation and refinement operations. Furthermore the use of large amounts of solvent also greatly encumbers the distillation of the filtrates.

A second important advantage of the two-time use of a considerable portion of the total amount of solvent required is therefore offered by the reduction of the total amount of filtrates to be processed by distillation. In the preferred case of the use of dilute aqueous acetic acid as washing liquid, the distillation of the filtrate is also considerably simplified, since only a relatively small portion of highly water-free acetic acid needs to be recovered as reaction medium, while most of the distillate can be separated in the form of dilute aqueous acetic acid and reused as washing liquid. The advantage of the process as regards the treatment of the filtrate is thus independent of the solubility of the target product, and applies also, therefore, to the production of aromatic monocarboxylic acids of relatively poor solubility in acetic acid.

The advantages of the process of the invention will be clarified by a number of examples. Thus, even the benzoic acid that is especially soluble in acetic acid can be obtained by this process as described in Examples 1 and 2, in a high purity and satisfactory yield by a technically very simple process. By reusing the washing filtrate of Example 1 for the dilution of the reaction mixture of Example 2, the yield was increased from 82 to 87 percent of the theory. If the washing filtrate of Example 2 is reused in the same manner, then only about 2 parts of filtrate would have to be processed by distillation per weight part of benzoic acid, and of these 2 parts only about 15% has to be isolated as low-moisture acetic acid for a subsequent oxidation batch.

In spite of relatively good solubility of benzoic acid in acetic acid media, the process of the invention thus offers the possibility of producing benzoic acid technically at low cost. Similar advantages of simplifying the reaction and the treatment of the reaction mixtures by adapting the concentration ratios in the reaction mixtures thereto can be achieved also in the oxidation of substituted toluenes, insofar as the substituents neither inhibit any oxidation reaction, nor are themselves oxidized under the reaction conditions, particularly with respect to the methyl group. Tertiary alkyl groups, halogens, aryl groups, aryloxy groups, alkyloxy groups and nitro groups could be considered as suitable substituents in this regard.

The advantage of the process of the invention becomes apparent especially in the case of a heavily contaminated starting product combined with high solubility of the target product, which is demonstrated by the example of the oxidation of a 92% pure p-tert-butyltoluene. Despite the considerable contamination of the starting product by the meta isomer and other impurities which commonly occur in the production of p-tert-butyltoluene and which are separable by distillation only with difficulty, and require a thorough washing of the target product, the p-tert-butylbenzoic acid can be obtained by the process of the invention with a purity of 99.9% in a yield of 95% of the theory.

The attainment of a satisfactory yield is especially difficult in the catalytic air oxidation of p-tert-butyltoluene in acetic acid solution on account of the high solubility of p-tert-butylbenzoic acid (24 g in 100 g of acetic acid at 24° C.). The solubility of the target product can be greatly reduced by diluting the acetic acid solution with water, but then the yield is increased at the cost of the purity, and the brown by-products discoloring the product constitute a problem difficult to solve; see the example given for comparison purposes, of the processing of the reaction mixture from the oxidation of p-tert-butyltoluene with atmospheric oxygen in acetic acid.

The process of the invention, due to the small amount of solution used during the reaction, and to the use of washing filtrates for the dilution of the reaction mixture required for the isolation of the product, offers a method which can be practiced technically with ease, and which, setting out from a p-tert-butyltoluene of low purity, permits the preparation of p-tertbutylbenzoic acid in both high purity and high yield. At the same time, less than 1.8 weight-parts of filtrates have to be distilled per weight-part of target product, and of this only less than 20% has to be obtained in the form of low-moisture acetic acid for reuse. If the dilution of the reaction mixture after completion of the oxidation is omitted, the reaction mixture resulting under the conditions of Examples 3 to 6 stiffens upon cooling to room temperature to an unfiltrable, solid mass.

The effect of the process of the invention that is so advantageous in cases such as the preparation of p-tert-butylbenzoic acid from a low-purity p-tert-butyltoluene is even more apparent in the oxidation of 2-chloro-4-tert-butyltoluene. This compound, which is obtainable by conventional methods through the chlorination of technical p-tert-butyltoluene on the nucleus, occurs as a mixture of several isomers. The product used in Examples 9 to 11 contained, after distillation, only 85.3% of 2-chloro-4-tert-butyltoluene plus 7.6% of 3-chloro-4-tert-butyltoluene, 5.2% of 2-chloro-5-tert-butyltoluene and 1.9% of additional impurities. The preparation of a pure 2-chloro-4-tert-butylbenzoic acid from this heavily contaminated starting product is made considerably more difficult by the especially high solubility of the aromatic carboxylic acid in acetic acid media, 13.4 g dissolving in 100 g of a 75% acetic acid at 22° C. Even under these unfavorable circumstances, the target product was obtained by the process of the invention in a yield of 85% of the theory.

In brief, the preferred embodiment of the invention involves the preparation of aromatic monocarboxylic acids by oxidation with oxygen or a gas containing oxygen of toluene or toluenes substituted in the nucleus, in the liquid phase, at a temperature of 80°–180° C. and a pressure of 5–50 bar in the presence of acetic acid as diluent and of one of the usual heavy metal catalysts. Preferred catalysts are soluble cobalt and/or manganese salts in combination with a bromide. The catalysts are preferably used at a molar ratio of the heavy metal catalyst to the alkyl aromatics to be oxidized, of 0.003:1 to 0.02:1 and a molar ratio of the bromide and heavy metal of 0.5:1 to 2:1, and the alkyl aromatic to be oxidized and the acetic acid are used in an approximate weight ratio of 0.5:1 to 6:1, preferably 1:1 to 3:1. After the reaction has ended, the mixture is diluted with 0.2 to 10, preferably 0.5 to 5, weight-parts of a suitable solvent or solvent mixture per weight part of the acetic acid used in the oxidation, to facilitate the isolation of the target product by solid-liquid separation of the cooled reaction mixture by one of the common separating processes.

EXAMPLES

The invention will be further explained by means of the following examples, without being restricted thereto.

EXAMPLE 1

A heated autoclave of Hastelloy C, equipped with stirrer, gas introduction tube, temperature sensor, pressure gauge and a pressurized reflux condenser was charged with 300 g of toluene, 100 g of acetic acid, 3 g of cobalt acetate tetrahydrate ($Co(OAc)_2.4H_2O$) and 1.5 g of sodium bromide. Through this mixture air was passed at 125°–130° C. and a pressure of 25 bar, with stirring, with a constant exhaust of 3 1/min. The reaction was observed by continuous measurement of the oxygen content in the exhaust gas. The end of the reaction 220 minutes later was manifested by the fact that the oxygen in the exhaust gas returned to the initial level of 21%. Then the passage of air was stopped, and, after the addition of 450 g of 50% acetic acid, the mixture was cooled to 23° C. with stirring. The crystalline target product was separated from the reaction mixture using a pressure filter, washed with 450 g of 50% acetic acid, and dried. 325.5 g of pure white benzoic acid was obtained.

EXAMPLE 2

The experiment described in Example 1 was repeated, but for the dilution of the reaction mixture after the end of the reaction, instead of the pure, 50% acetic acid, the washing filtrate (504 g) obtained in Example 1 in the washing of the target product and recovered separately from the reaction mother liquor was used. Processing as in the preceding experiment resulted in 346.5 g of pure white benzoic acid of a purity of 99.7%.

EXAMPLE 3

Analogously to Example 1, 300 g of p-tert-butyltoluene (93.3% pure) was oxidized in the presence of 50 g of acetic acid, 3 g of cobalt acetate tetrahydrate and 1.5 g of sodium bromide at 25 bar and 115°–135° C. by passing air through it to produce a gas exhaust rate of 1.5 liters per minute. The oxygen absorption ended after a reaction period of 300 minutes; then 450 g of 74.5% acetic acid was added, the dilute reaction mixture was cooled with stirring to room temperature and filtered, and the crystallizate was washed with 450g of 70% acetic acid. 311.5 g of p-tert-butylbenzoic acid resulted, in the form of white crystals of a purity of 99.6 percent by weight as determined by gas chromatography, with a terephthalic acid content of 0.16%.

EXAMPLE 4

Example 3 was repeated, doubling the amount of acetic acid to 100 g, at a reaction temperature of 90° to 110° C., a gas exhaust rate of 1.7 1/min, and a reaction time of 250 minutes. The reaction mixture was diluted with 450 g of 70% acetic acid and the target product was isolated and purified as described in Example 3, the washing filtrate (464.5 g) being recovered separately from the mother liquor (579.5 g). The test yielded 311 g of p-tert-butylbenzoic acid in the form of pure white crystals with a purity of more than 99.8% at a terephthalic acid content of less than 0.02%.

EXAMPLE 5

The previously described experiment was repeated, but for the dilution of the reaction mixture at the end of the reaction, the washing filtrate obtained in Example 4 was used instead of the 450 g of 70% acetic acid. The yield of pure white p-tert-butylbenzoic acid amounted to 320 g with a purity of 99.9%.

EXAMPLE 6

Analogously to the preceding experiments, 400 g of p-tert-butyltoluene is oxidized in the presence of 200 g of acetic acid, 4 g of cobalt acetate tetrahydrate and 2 g of sodium bromide at 100°–150° C. and at a gas exhaust rate of 3 1/min, within 180 minutes. The reaction mixture is diluted with 600 g of 73% acetic acid and cooled to 25° C. The target product was isolated in the usual manner and washed successively with 600 g of 73% acetic acid and hot water (80° C.) The result was 404.5 g of p-tert-butylbenzoic acid as pure white crystals of a purity of 99.9%.

Example for Purposes of Comparison

Using 300 g of p-tert-butyltoluene (93.3% pure), 400 g of acetic acid, 25 g of cobalt acetate tetrahydrate and 2 g of ammonium bromide the oxidation was performed in the manner described above, at 115°–130° C. at a gas exhaust rate of 3 1/min. After the oxidation had ended, 135 g of water was added. The reaction mixture thus diluted was cooled, with stirring, to 25° C., filtered, and the filter cake washed twice with 100 g of 70% acetic acid and once with 100 g of water, and then dried. 299 g of brownish colored product was obtained, with a purity of 99.2%.

EXAMPLE 7

Analogously to Example 1, 300 g of o-chlorotoluene was oxidized in the presence of 100 g of acetic acid, 3 g of cobalt acetate tetrahydrate and 1.5 g of sodium bromide at a pressure of 25 bar, a temperature of 110°–130° C., and a gas exhaust rate of 3 1/min. After the oxidation had ended, 450 g of 50% acetic acid was added, the mixture was cooled to 25° C. and filtered, and the filter cake was washed with 750 g of 50% acetic acid, the mother liquor (314.5 g) and washing filtrates (693.5 g) being recovered separately. The dried filter cake yielded 318.5 g of o-chlorobenzoic acid.

EXAMPLE 8

The experiment described in Example 7 was repeated, but after the reaction had ended the reaction mixture was diluted with 660 g of the washing filtrate from the preceding experiment, and the filter cake was washed with only 600 g of 50% acetic acid. 335.5 g of o-chlorobenzoic acid was obtained.

EXAMPLE 9

Analogously to Example 1, 2-chloro-4-tert-butyltoluene was oxidized, which has been obtained by chlorination on the nucleus of a technical p-tert-butyltoluene using anhydrous ferric chloride as catalyst. The chlorination product, after purification by distillation, contained only 85.3% of 2-chloro-4-tert-butyltoluene, plus 7.6% of 3-chloro-4-tert-butyltoluene, 5.2% of 2-chloro-5-tert-butyltoluene and 1.9% of other impurities. 350 g of this product mixture was oxidized within 130 minutes at 130° C. at 25 bar by passing air through it at an exhaust rate of 3 l/min, after the addition of 100 g of acetic acid, 3 g of cobalt acetate tetrahydrate and 1.5 g of sodium bromide. After the reaction had ended the mixture was diluted with 275 g of acetic acid and 225 g of water, cooled with stirring to 3° C. and filtered, and the filter cake was washed with 500 g of a 55% acetic acid at 3° C. and dried in the air stream. 349 g of yellow reaction product was obtained, having a melting range of 98° to 108° C. and a purity determined by gas chromatography of 96.9%.

EXAMPLE 10

The experiment described in Example 9 was repeated at slightly reduced reaction temperature of 125° C. under modified product processing conditions. After the oxidation ended, only 225 g of acetic acid and 75 g of water was added in this case. After filtration of the diluted reaction mixture cooled to 3° C., the product was washed with 300 g of 75% acetic acid at 3° C., the mother liquor (419.5 g) and washing filtrate (360 g) being recovered separately. The resulting product was 271 g of 2-chloro-4-tert-butylbenzoic acid in the form of a white crystallizate with a melting point of 117° C. and a purity determined by gas chromatography of 99.5%.

EXAMPLE 11

Example 10 was repeated using 355 g of the washing filtrate obtained therein for the dilution of the reaction mixture after the reaction had ended. 296 g of 2-chloro-4-tert-butylbenzoic acid was obtained, having the same quality as in Example 10.

EXAMPLE 12

Similarly to Example 1, 200 g of p-phenoxytoluene was oxidized within 95 minutes in the presence of 200 g of acetic acid, 3 g of cobalt acetate tetrahydrate and 1.5 g of sodium bromide at a pressure of 25 bar, a gas exhaust rate of 3 l/min, and a temperature of 110°–115° C.

After the reaction ended, the oxidation mixture stiffened to a solid mass upon cooling to room temperature. It was diluted with 400 g of 90% acetic acid, heated to the refluxing temperature, and the clear solution that resulted was cooled, with stirring, to room temperature. The stirrable and fluid suspension then obtained was filtered and the filter cake washed with 400 g of 90% acetic acid, the mother liquor (530 g) and the washing filtrate (433.5 g) being recovered separately. The dried filter cake yielded 204 g of p-phenoxybenzoic acid of a purity of 99.9%.

EXAMPLE 13

The experiment described in Example 12 was repeated, but the 433.5 g of washing filtrate from Example 12 was used for diluting the reaction mixture after the oxidation had ended, instead of the 400 g of 90% acetic acid. The experiment resulted in a yield of 209.5 g of p-phenoxybenzoic acid of a purity of 99.9%.

EXAMPLE 14

Example 12 was repeated using 400 g of p-phenoxytoluene, 300 g of acetic acid, 5 g of cobalt acetate tetrahydrate and 2.5 g of sodium bromide at a reaction temperature of 118°–125° C. and a reaction time of 150 minutes, but when the oxidation had ended, 700 g of 80% acetic acid was used for diluting the reaction mixture and again for washing out the target product after the pressure filtration. The result was 419.5 g of p-phenoxybenzoic acid of the same purity as in the two experiments previously described.

EXAMPLE 15

Example 14 was repeated using the 693.5 g of washing filtrate obtained therein, for the purpose of diluting the reaction mixture after the reaction had ended; 425.5 g of pphenoxybenzoic acid was obtained with a purity of 99.9%.

EXAMPLE 16

Similarly to Example 1, 250 g of m-nitrotoluene was oxidized in the presence of 150 g of acetic acid, 4.5 g of cobalt acetate tetrahydrate and 2 g of sodium bromide at a pressure of 25 bar, a temperature of 135°–145° C. and a gas exhaust rate of 3 l/min, within a period of 200 minutes. The reaction mixture, diluted with 400 g of 69% acetic acid, was cooled to 5° C. with stirring, filtered, twice washed with 125 g of 50% acetic acid at 5° C. and once with 150 g of water, the mother liquor (514.5 g) and the combined washing filtrates (441 g) being recovered separately. After drying, 230 g of m-nitrobenzoic acid was obtained.

EXAMPLE 17

The experiment described as Example 16 was repeated, using the 441 g of washing filtrate from that experiment for diluting the reaction mixture after the oxidation had ended. 245 g of m-nitrobenzoic acid was obtained.

It will be understood that the specification and examples are illustrative but not limitative of the present invention and that other embodiments within the spirit and scope of the invention will suggest themselves to those skilled in the art.

What is claimed is:

1. In a process for the preparation of aromatic monocarboxylic acid by the oxidation of a liquid phase alkylaromatic compound selected from toluene and toluene substituted in its ring with halogen, aryl groups, nitro groups, alkoxy groups, aryloxy groups and tertiary alkyl groups using oxygen or gas containing oxygen, and a heavy metal catalyst
the steps consisting essentially of:
oxidizing the aromatic compound in a 0.5:1 to 6:1 weight ratio mixture with acetic acid using the oxygen or the gas containing oxygen, at a temperature of about 80? C. to about 180° C., at a pressure of 5–50 bar, in the presence of the catalyst in a molar ratio of about 0.003:1 to about 0.02:1 catalyst to alkyl aromatic, and in the presence of a bromide added in a molar ratio of bromide to heavy metal of 0.5:1 to 2:1; thereafter diluting the reaction mixture with 0.2 to 10 weight parts of dilute aqueous acetic acid per weight acetic acid used during the oxidation; and, thereafter cooling and separating, by a solid-liquid separation method, the solid product from the reaction mixture.

2. The process of claim 1 wherein the ratio of aromatic compound to acetic acid is about 1:1 to 3:1.

3. The process of claim 1 wherein the ratio of dilute aqueous acetic acid to acetic acid is about 0.5 to 5.

4. The process of claim 1 wherein, after the diluting of the reaction mixture the reaction mixture is adjusted to a temperature of 80°–180° C.

5. The process of claim 1 wherein said heavy metal catalyst is selected from soluble salts of cobalt and manganese, and the bromide is selected from sodium bromide, ammonium bromide.

6. The process of claim 1 wherein the acid prepared is p-tert-butylbenzoic acid, and the aromatic compound is p-tert-butyl-toluene.

7. The process of claim 1 wherein the acid prepared is p-phenoxybenzoic acid and the aromatic compound is p-phenoxytoluene.

8. The process of claim 1 wherein acid prepared is o-chlorobenzoic acid and the aromatic compound is o-chlorotoluene.

9. The process of claim 1 wherein the acid prepared is m-nitrobenzoic acid and the aromatic compound is m-nitrotoluene.

10. The process of claim 1 wherein the aromatic compound is selected from toluene, p-tert-butyltoluene, p-phenoxytoluene, o-chlorotoluene and m-nitrotoluene.

11. The process of claim 5 wherein the aromatic compound is selected from toluene, p-tert-butyltoluene, p-phenoxytoluene, o-chlorotoluene and m-nitrotoluene.

12. The process of claim 1 wherein a washing filtrate from a previous oxidation run with identical starting products is used for dilution of the reaction mixture after completion of the reaction.

13. The process of claim 14, wherein said heavy metal catalyst is selected from soluble salts of cobalt and manganese, and the bromide is selected from sodium bromide, or ammonium bromide.

14. The process of claim 14, wherein the aromatic compound is selected from toluene, p-tert-butyltoluene, p-phenoxytoluene, o-chlorotoluene and m-nitrotoluene.

* * * * *

UNITED STATES PATENT AND TRADEMARK OFFICE
CERTIFICATE OF CORRECTION

PATENT NO. : 4,603,220
DATED : July 29, 1986
INVENTOR(S) : Marcel Feld

It is certified that error appears in the above-identified patent and that said Letters Patent is hereby corrected as shown below:

Column 2, line 30, "Auslegesqhrift" should be --Auslegeschrift--

Column 2, line 46, "41,253 77" should be --41,253/77--

Column 4, line 8, between "to be" and "product" should read
--selected such that no precipitation of previously dissolved--

Column 12, line 21, "14" should be --12--

Column 12, line 25, "14" should be --12--

Signed and Sealed this

Fifteenth Day of September, 1987

Attest:

DONALD J. QUIGG

Attesting Officer

Commissioner of Patents and Trademarks